(12) United States Patent
Rapoport (10) Patent No.: US 9,155,490 B2
(45) Date of Patent: Oct. 13, 2015

(54) INTEGRATED STETHOSCOPE-METAL DETECTOR DEVICE

(71) Applicant: ASPECT IMAGING LTD., Shoham (IL)

(72) Inventor: Uri Rapoport, Moshav Ben Shemen (IL)

(73) Assignee: ASPECT IMAGING LTD., Shoham (IL)

(*) Notice: Subject to any disclaimer, the term of this patent is extended or adjusted under 35 U.S.C. 154(b) by 170 days.

(21) Appl. No.: 13/788,759

(22) Filed: Mar. 7, 2013

(65) Prior Publication Data

US 2014/0257081 A1 Sep. 11, 2014

(51) Int. Cl.
| | |
|---|---|
| A61B 5/05 | (2006.01) |
| A61B 5/06 | (2006.01) |
| A61B 5/00 | (2006.01) |
| A61B 7/02 | (2006.01) |
| A61B 7/00 | (2006.01) |

(52) U.S. Cl.
CPC . *A61B 5/062* (2013.01); *A61B 5/05* (2013.01); *A61B 5/742* (2013.01); *A61B 5/7405* (2013.01); *A61B 5/7455* (2013.01); *A61B 7/00* (2013.01); *A61B 7/02* (2013.01)

(58) Field of Classification Search
CPC ........ A61B 5/05; A61B 5/062; A61B 5/7405; A61B 5/742; A61B 5/7455; A61B 7/00; A61B 7/02
See application file for complete search history.

(56) References Cited

U.S. PATENT DOCUMENTS

| | | | | | |
|---|---|---|---|---|---|
| 4,334,192 | A | * | 6/1982 | Podhrasky | 324/329 |
| 5,329,944 | A | * | 7/1994 | Fabian et al. | 128/899 |
| 5,959,451 | A | * | 9/1999 | De Torfino | 324/236 |
| 8,851,018 | B2 | | 10/2014 | Rapoport et al. | |
| 8,896,310 | B2 | | 11/2014 | Rapoport | |
| 2004/0178794 | A1 | * | 9/2004 | Nelson | 324/323 |
| 2011/0162652 | A1 | | 7/2011 | Rapoport | |
| 2011/0186049 | A1 | | 8/2011 | Rapoport | |
| 2011/0234347 | A1 | | 9/2011 | Rapoport | |
| 2011/0304333 | A1 | | 12/2011 | Rapoport | |
| 2012/0071745 | A1 | | 3/2012 | Rapoport | |
| 2012/0073511 | A1 | | 3/2012 | Rapoport et al. | |
| 2012/0077707 | A1 | | 3/2012 | Rapoport | |
| 2012/0119742 | A1 | | 5/2012 | Rapoport | |
| 2013/0066136 | A1 | * | 3/2013 | Palese et al. | 600/11 |
| 2013/0079624 | A1 | | 3/2013 | Rapoport | |
| 2013/0109956 | A1 | | 5/2013 | Rapoport | |
| 2013/0237803 | A1 | | 9/2013 | Rapoport | |
| 2013/0328559 | A1 | | 12/2013 | Rapoport | |

(Continued)

OTHER PUBLICATIONS

Aspect Imaging Ltd., "Shutting Assembly for Closing an Entrance of an MRI Device", co-pending U.S. Appl. No. 14/540,163, filed Nov. 13, 2014.

(Continued)

*Primary Examiner* — Ruth S Smith (57) ABSTRACT

An integrated metal detector-portable medical device adapted to identify metals in a human body, where the metal detector is in connection with the portable medical device. The metal detector includes: at least one transmitter adapted to induce a magnetic field generated by a metal; at least one sensor adapted to detect the magnetic field generated by the metals to be detected; and at least one signaling mechanism adapted, upon detection of a magnetic field, to alert the user of identification of metals, if the intensity of a magnetic field is above a predetermined value.

10 Claims, 4 Drawing Sheets

(56) References Cited

U.S. PATENT DOCUMENTS

| | | |
|---|---|---|
| 2013/0328560 A1 | 12/2013 | Rapoport |
| 2013/0328563 A1 | 12/2013 | Rapoport |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0378821 A1 | 12/2014 | Rapoport et al. |
| 2014/0378825 A1 | 12/2014 | Rapoport et al. |
| 2015/0065788 A1 | 3/2015 | Rapoport |

OTHER PUBLICATIONS

Aspect Imaging Ltd, "MRI—Incubator's Closure Assembly", co-pending U.S. Appl. No. 14/539,442, filed Nov. 12, 2014.

Aspect Imaging Ltd., "Cage in an MRD with a Fastening/Attenuating System", co-pending U.S. Appl. No. 14/527,950, filed Oct. 30, 2014.

Rapoport, Uri, "RF Shielding Conduit in an MRI Closure Assembly", co-pending U.S. Appl. No. 14/574,785, filed Dec. 18, 2014.

Aspect Imaging Ltd., "System and Method for Generating Invasively Hyperpolarized Images", co-pending U.S. Appl. No. 14/556,682, filed Dec. 1, 2014.

Aspect Imaging Ltd., "System and Method for Generating Invasively Hyperpolarized Images", co-pending U.S. Appl. No. 14/556,654, filed Dec. 1, 2014.

Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.

Aspect Imaging Ltd., "Chamber for Housing Animals During Anaesthetic Procedures", co-pending U.S. Appl. No. 14/537,266, filed Nov. 10, 2014.

Aspect Imaging Ltd., "RF Automated Tuning System Used in a Magnetic Resonance Device and Methods Thereof", co-pending U.S. Appl. No. 14/588,741, filed Jan. 2, 2015.

Aspect Imaging LTD., "Means for Operating an MRI Device Within a RF-Magnetic Environment", co-pending U.S. Appl. No. 14/596,320, filed Jan. 14, 2015.

Aspect Imaging Ltd., "Means and Method for Operating an MRI Device Within a RF-Magnetic Environment", co-pending U.S. Appl. No. 14/596,329, filed Jan. 14, 2015.

Aspect Imaging Ltd., "CT/MRI Integrated System for the Diagnosis of Acute Strokes and Methods Thereof", co-pending U.S. Appl. No. 14/598,517, filed Jan. 16, 2015.

Aspect Imaging Ltd., "Mechanical Clutch for MRI", co-pending U.S. Appl. No. 14/611,379, filed Feb. 2, 2015.

Aspect Imaging Ltd., "Method for Providing High Resolution, High Contrast Fused MRI Images", co-pending U.S. Appl. No. 13/877,533, filed May 22, 2014.

Aspect Imaging Ltd., "Method for Manipulating the MRI's Protocol of Pulse-Sequences", co-pending U.S. Appl. No. 14/070,695, filed Nov. 4, 2013.

Aspect Imaging Ltd., "Foamed Patient Transport Incubator", co-pending U.S. Appl. No. 14/531,289, filed Nov. 3, 2014.

Aspect Imaging Ltd., "Incubator Deployable Multi-Functional Panel", co-pending U.S. Appl. No. 14/619,557, filed Feb. 11, 2015.

Aspect Imaging Ltd., "MRI Thermo-Isolating Jacket", co-pending U.S. Appl. No. 14/623,039, filed Feb. 16, 2015.

Aspect Imaging Ltd., "MRI RF Shielding Jacket", co-pending U.S. Appl. No. 14/623,051, filed Feb. 16, 2015.

Aspect Imaging Ltd., "Capsule for a Pneumatic Sample Feedway", co-pending U.S. Appl. No. 14/626,391, filed Feb. 19, 2015.

Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.

Aspect Imaging Ltd., "Temperature-Controlled Exchangeable NMR Probe Cassette and Methods Thereof", co-pending U.S. Appl. No. 14/504,890, filed Oct. 2, 2014.

Aspect Imaging Ltd., "NMR Extractable Probe Cassette Means and Methods Thereof", co-pending U.S. Appl. No. 14/504,907, filed Oct. 2, 2014.

\* cited by examiner

INTEGRATED STETHOSCOPE-METAL DETECTOR DEVICE

FIELD OF THE INVENTION

The present invention generally pertains to means and methods for screening subjects for metal containing objects inside them, and more specifically, the invention relates to medical devices, such as stethoscopes and endoscopes especially adapted to treat gossypiboma and to methods thereof.

BACKGROUND OF THE INVENTION

MRI machines produce magnetic force measured in tesla (T), a unit of magnetic flux. Most MRI machines range between 1.0 T to 1.5 T, with more powerful units at 3.0 T. There are two features of a magnetic field that are the source of most MRI incidents: (1) projectile (missile effect) and (2) translational attraction. The projectile effect causes ferrous-based materials, nickel alloys and most stainless to be pulled violently toward the magnetic source. Translational attraction occurs when one point of an object in a magnetic field is attracted to a greater extent than the object's furthest point from the attracting source. This differential creates a more forceful attraction, increasing the speed with which the object may move toward the magnetic source.

These effects make all metal containing objects highly dangerous in the MRI environment. For example A hairpin or paper clip within the 1-3 T line range could reach a velocity of 40 mph and will be attracted to the center of the generated field (x, y and z axis) where the lines of force are equal.

All pacemakers and implantable cardioverter/defibrillators should be considered contraindicated under any circumstance in the MRI room. When these devices are exposed to an MRI environment, a life-threatening condition may be created within the 3 T line. Intravascular catheters, intubation equipment, infusion pumps, orthopedic implants, stents and other devices should be verified as MRI-safe in the prescreening.

All patients, visitors, parents/guardians of patients and MRI hospital personnel must pass through an MRI screening process for entering the MRI room. To date, the screening process includes questioning of the subject about to enter the MRI room. Questioning is an important source of information but not always reliable. This method depend on communication skills and memory of the subject that are not always adequate to ensure safety. In addition to that there is the possibility that responsible personnel forget to question a patient about metals attached to him.

Thus there remains a long felt need for a reliable objective method for screening subjects prior their entrance to the MRI room that are not based on communicating with the subject. In addition, this method should be carried out in parallel to another action so that it will not be dependent on the memory of a staff person.

SUMMARY OF THE INVENTION

It is one object of the present invention to provide an integrated metal detector-portable medical device adapted to identify metals in a human body, wherein the metal detector is embedded within the portable medical device. It is acknowledged in this respect that the term "embedded within" further refers to terms as follows: "incorporated with", "comprises" and otherwise "provided in remote or physical connection with".

It is another object of the present invention to provide a metal detector for identifying metals in a human body, comprising: at least one transmitting means adapted to induce magnetic field generated by the metals to be detected; at least one sensor adapted to detect the magnetic field generated by the metals to be detected; and at least one signaling means adapted, upon detection of the magnetic field, to alert the identification of the metals, if the intensity of the magnetic field is above a predetermined value; wherein the metal detector is embedded within a portable medical device.

It is another object of the present invention to provide the metal detector as defined above, wherein the at least one signaling means adapted, upon detection of the magnetic field, to alert the identification of the metals, if the flux of the magnetic field is above a predetermined value.

It is another object of the present invention to provide the metal detector as defined above, wherein the transmitting means are adapted to generate a second magnetic field so as to induce the magnetic field generated by the metal.

It is another object of the present invention to provide the metal detector as defined above, wherein the sensor is at least one radiometer.

It is another object of the present invention to provide the metal detector as defined above, wherein the transmitting means is an antenna or a conductive coil.

It is another object of the present invention to provide the metal detector as defined above, wherein the metal detector comprises at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is another object of the present invention to provide the metal detector as defined above, additionally comprising processing means in communication with the first sensor, second sensor and the third sensor, adapted to analyze the first direction, X, second direction, Y, and the third direction, Z so as to determine the 3D position of the metals.

It is another object of the present invention to provide the metal detector as defined above, wherein the 3D position of the metals comprises parameters selected from a group consisting of the 2D location, depth, of the metals from the surface of the human body.

It is another object of the present invention to provide the metal detector as defined above, wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is another object of the present invention to provide the metal detector as defined above, wherein the signal is at least one signal selected from a group consisting of (a) audible signal, (b) visual signal, (c) sensual signal, vibration, and any combination thereof.

It is another object of the present invention to provide the metal detector as defined above, wherein the intensity of the signal is in function of at least one parameter selected from a group consisting of depth, d, of the metals from the surface of the human body, the type of the metal, the quantity of the metals and any combination thereof.

It is another object of the present invention to provide the metal detector as defined above, wherein the portable medical device is a stethoscope.

It is another object of the present invention to provide the metal detector as defined above, wherein the stethoscope comprises at least one chest piece (1), reversibly in contact with the human body; at least one ear tip (2); and a tubing (3) connecting the same.

It is another object of the present invention to provide the metal detector as defined above, wherein the at least one sensor is embedded within at least one selected from a group consisting of the chest piece, the ear tip, the tubing and a combination thereof.

It is another object of the present invention to provide the metal detector as defined above, wherein the at least one signaling means is embedded within at least one selected from a group consisting of the chest piece, the ear tip, the tubing and a combination thereof such that the signal is being activated within the same.

It is another object of the present invention to provide the metal detector as defined above, wherein the signaling means is adapted to alert on detected metals located underneath the surface of a human body.

It is another object of the present invention to provide the metal detector as defined above, wherein the transmitting means comprise means for generating a pulsed magnetic field.

It is another object of the present invention to provide the metal detector as defined above, additionally comprising marking means adapted to mark the surface of the body.

It is another object of the present invention to provide the metal detector as defined above, additionally comprising at least one display for providing a visual indication of the position of the metals in the x-y plane.

It is another object of the present invention to provide the metal detector as defined above, additionally comprising at least one display for providing a visual indication of the position of the metals in the x-y-z planes.

It is another object of the present invention to provide a stethoscope, comprising: at least metal detector, comprising: at least one transmitting means adapted to induce magnetic field generated by the metals to be detected; at least one sensor adapted to detect the magnetic field generated by the metals to be detected; at least one signaling means adapted, upon detection of the magnetic field, to alert the identification of the metals, if the intensity of the magnetic field is above a predetermined value; wherein the metal detector is embedded within the stethoscope.

It is another object of the present invention to provide the stethoscope as defined above, wherein the stethoscope comprises at least one chest piece (1), reversibly in contact with the human body; at least one ear tip (2); and tubing (3) connecting the same.

It is another object of the present invention to provide the stethoscope as defined above, wherein the at least one signaling means adapted, upon detection of the magnetic field, to alert the identification of the metals, if the flux of the magnetic field is above a predetermined value.

It is another object of the present invention to provide the stethoscope as defined above, wherein the transmitting means are adapted to generate a second magnetic field so as to induce the magnetic field generated by the metal.

It is another object of the present invention to provide the stethoscope as defined above, wherein the sensor is at least one radiometer.

It is another object of the present invention to provide the stethoscope as defined above, wherein the transmitting means is an antenna or a conductive coil.

It is another object of the present invention to provide the stethoscope as defined above, wherein the metal detector comprises at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is another object of the present invention to provide the stethoscope as defined above, additionally comprising processing means in communication with the first sensor, second sensor and the third sensor, adapted to analyze the first direction, X, second direction, Y, and the third direction, Z so as to determine the 3D position of the metals.

It is another object of the present invention to provide the stethoscope as defined above, wherein the 3D position of the metals comprises parameters selected from a group consisting of the 2D location, depth, d, of the metals from the surface of the human body.

It is another object of the present invention to provide the stethoscope as defined above, wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is another object of the present invention to provide the stethoscope as defined above, wherein the signal is at least one signal selected from a group consisting of (a) audible signal, (b) visual signal, (c) sensual signal, vibration, and any combination thereof.

It is another object of the present invention to provide the stethoscope as defined above, wherein the intensity of the signal is in function of at least one parameter selected from a group consisting of depth, d, of the metals from the surface of the human body, the type of the metal, the quantity of the metals and any combination thereof.

It is another object of the present invention to provide the stethoscope as defined above, wherein the at least one sensor is embedded within at least one selected from a group consisting of the chest piece, the ear tip, the tubing and a combination thereof.

It is another object of the present invention to provide the stethoscope as defined above, wherein the at least one signaling means is embedded within at least one selected from a group consisting of the chest piece, the ear tip, the tubing and a combination thereof such that the signal is being activated within the same.

It is another object of the present invention to provide the stethoscope as defined above, wherein the signaling means is adapted to alert on detected metals located underneath the surface of a human body.

It is another object of the present invention to provide the stethoscope as defined above, wherein the transmitting means comprise means for generating a pulsed magnetic field.

It is another object of the present invention to provide the stethoscope as defined above, additionally comprising marking means adapted to mark the surface of the body.

It is another object of the present invention to provide the stethoscope as defined above, additionally comprising at least one display for providing a visual indication of the position of the metals in the x-y plane.

It is another object of the present invention to provide the stethoscope as defined above, additionally comprising at least one display for providing a visual indication of the position of the metals in the x-y-z planes.

It is another object of the present invention to provide a portable medical device (100) for the prevention of gossypiboma, comprising a distal end and a proximal end interconnect to each other; at least one metal detector for identifying metals underneath a surface of a human body, comprising: at least one transmitting means adapted to induce magnetic field generated by the metals to be detected; at least one sensor adapted to detect the magnetic field generated by the metals to be detected; at least one signaling means; wherein the at least one transmitting means and/or the at least one sensor are embedded either within the distal end or the proximal end; further wherein the signaling means adapted, upon detection of the magnetic field, to alert the identification of the metals, if the intensity of the magnetic field generated is above a predetermined value so as to prevent gossypiboma.

It is another object of the present invention to provide the portable medical device as defined above, selected from a group consisting of a stethoscope, endoscope and a surgical item, disposable items—sponges, needles, tapes; non-disposable items—graspers, forceps, clamps, occluders, retractors, ribs and other tissue distractors, positioners, stereotactic devices, mechanical cutters scalpels, lancets, drill bits, rasps, trocars, ligasure, harmonic scalpel, dilators and specula, suction tips and tubes, sealing devices, surgical staplers, irrigation and injection needles, tips and tubes, tyndallers, drills, dermatomes; and any combination thereof It is another object of the present invention to provide the portable medical device as defined above, wherein the portable medical device wherein the proximal end is located outside the human body and the distal end is reversibly inserted within the body.

It is another object of the present invention to provide the portable medical device as defined above, wherein the portable medical device additionally comprising detectable metal indicia embedded within or on the surface of the same; the metal tag is being identified by the metal detector during or after a medical procedure so as to prevent Gossypiboma.

It is another object of the present invention to provide the portable medical device as defined above, wherein the at least one signaling means adapted, upon detection of the magnetic field, to alert the identification of the metals, if the flux of the magnetic field is above a predetermined value.

It is another object of the present invention to provide the portable medical device as defined above, wherein the transmitting means are adapted to generate a second magnetic field so as to induce the magnetic field generated by the metal.

It is another object of the present invention to provide the portable medical device as defined above, wherein the sensor is at least one radiometer.

It is another object of the present invention to provide the portable medical device as defined above, wherein the transmitting means is an antenna or a conductive coil.

It is another object of the present invention to provide the portable medical device as defined above, wherein the metal detector comprises at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is another object of the present invention to provide the portable medical device as defined above, additionally comprising processing means in communication with the first sensor, second sensor and the third sensor, adapted to analyze the first direction, X, second direction, Y, and the third direction, Z so as to determine the 3D position of the metals.

It is another object of the present invention to provide the portable medical device as defined above, wherein the 3D position of the metals comprises parameters selected from a group consisting of the 2D location, depth, d, of the metals from the surface of the human body.

It is another object of the present invention to provide the portable medical device as defined above, wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is another object of the present invention to provide the portable medical device as defined above, wherein the signal is at least one signal selected from a group consisting of (a) audible signal, (b) visual signal, (c) sensual signal, vibration, and any combination thereof.

It is another object of the present invention to provide the portable medical device as defined above, wherein the intensity of the signal is in function of at least one parameter selected from a group consisting of depth, d, of the metals from the surface of the human body, the type of the metal, the quantity of the metals and any combination thereof.

It is another object of the present invention to provide the portable medical device as defined above, wherein the signaling means is adapted to alert on detected metals located underneath the surface of a human body.

It is another object of the present invention to provide the portable medical device as defined above, wherein the transmitting means comprise means for generating a pulsed magnetic field.

It is another object of the present invention to provide the portable medical device as defined above, additionally comprising marking means adapted to mark the surface of the body.

It is another object of the present invention to provide the portable medical device as defined above, additionally comprising at least one display for providing a visual indication of the position of the metals in the x-y plane.

It is another object of the present invention to provide the portable medical device as defined above, additionally comprising at least one display for providing a visual indication of the position of the metals in the x-y-z planes.

It is another object of the present invention to provide a method for preventing gossypiboma, comprises steps of: providing a metal detector comprising: at least one transmitting means adapted to induce magnetic field generated by the metals to be detected; at least one sensor; at least one signaling means; inducing, during the medical procedure, a magnetic field to be generated by the metals to be detected; sensing the magnetic field; if the intensity of the magnetic field is above a predetermined threshold, identifying the presence of the detectable metals by the magnetic sensor; sending a signal, thereby alerting the detection of the detectable metals;

wherein the step of providing the metal detector further comprising step of embedding the metal detector within a portable medical device It is another object of the present invention to provide a method for identifying detectable metals in a human body, comprises steps of: providing a metal detector comprising: at least one transmitting means adapted to induce magnetic field generated by the metals to be detected; at least one sensor; at least one signaling means; inducing, during the medical procedure, a magnetic field to be generated by the metals to be detected; sensing the magnetic field; if the intensity of the magnetic field is above a predetermined threshold, identifying the presence of the detectable metals by the magnetic sensor; sending a signal, thereby alerting the detection of the detectable metals; wherein the step of providing the metal detector further comprising step of embedding the metal detector within a portable medical device.

It is another object of the present invention to provide the method as defined above, additionally comprising step of generating magnetic field in the vicinity of the metals to be detected thereby inducing the magnetic field generated by the metals to be detected.

It is another object of the present invention to provide the method as defined above, wherein the step of generating magnetic field is performed by at least one selected from a group consisting of pulsed magnetic field or an alternating magnetic field, thereby inducing currents within the metals to be detected, thereby generating the magnetic field.

It is another object of the present invention to provide the method as defined above, wherein the at least one signaling means adapted, upon detection of the magnetic field, to alert the identification of the metals, if the flux of the magnetic field is above a predetermined value.

It is another object of the present invention to provide the method as defined above, additionally comprising step of generating a second magnetic field so as to induce the magnetic field generated by the metal.

It is another object of the present invention to provide the method as defined above, additionally comprising step of selecting the sensor to be at least one radiometer.

It is another object of the present invention to provide the method as defined above, additionally comprising step of selecting the transmitting means from a group consisting of antenna, a conductive coil; and any combination thereof.

It is another object of the present invention to provide the method as defined above, additionally comprising step of providing the metal detector with at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is another object of the present invention to provide the method as defined above, additionally comprising step of providing processing means in communication with the first sensor, second sensor and the third sensor, adapted to analyze the first direction, X, second direction, Y, and the third direction, Z so as to determine the 3D position of the metals.

It is another object of the present invention to provide the method as defined above, wherein the 3D position of the metals comprises parameters selected from a group consisting of the 2D location, depth, d, of the metals from the surface of the human body.

It is another object of the present invention to provide the method as defined above, wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is another object of the present invention to provide the method as defined above, wherein the signal is at least one signal selected from a group consisting of (a) audible signal, (b) visual signal, (c) sensible signal, and any combination thereof.

It is another object of the present invention to provide the method as defined above, wherein the intensity of the signal is in function of at least one parameter selected from a group consisting of depth of the metals from the surface of the human body, the type of the metal, the quantity of the metals and any combination thereof.

It is another object of the present invention to provide the method as defined above, wherein the portable medical device is a stethoscope.

It is another object of the present invention to provide the method as defined above, wherein the stethoscope comprises at least one chest piece (1), reversibly in contact with the human body; at least one ear tip (2); and tubing (3) connecting the same.

It is another object of the present invention to provide the method as defined above, wherein the at least one sensor is embedded within at least one selected from a group consisting of the chest piece, the ear tip, the tubing and a combination thereof.

It is another object of the present invention to provide the method as defined above, wherein the at least one signaling means is embedded within at least one selected from a group consisting of the chest piece, the ear tip, the tubing and a combination thereof such that the signal is being activated within the same.

It is another object of the present invention to provide the method as defined above, wherein the signaling means is adapted to alert on detected metals located underneath the surface of a human body.

It is another object of the present invention to provide the method as defined above, wherein the transmitting means comprise means for generating a pulsed magnetic field.

It is another object of the present invention to provide the method as defined above, additionally comprising marking means adapted to mark the surface of the body.

It is still an object of the present invention to provide the method as defined above, additionally comprising at least one display for providing a visual indication of the position of the metals in the x-y plane.

It is lastly an object of the present invention to provide the method as defined above, additionally comprising at least one display for providing a visual indication of the position of the metals in the x-y-z planes.

BRIEF DESCRIPTION OF THE FIGURES

In order to better understand the invention and its implementation in practice, a plurality of embodiments will now be described, by way of non-limiting example only, with reference to the accompanying drawings, wherein FIG. 1 schematically illustrates a schematic view of the present invention (100).

DETAILED DESCRIPTION OF THE PREFERRED EMBODIMENTS

The following description is provided, alongside all chapters of the present invention, so as to enable any person skilled in the art to make use of the invention and set forth the best modes contemplated by the inventor of carrying out this invention. Various modifications, however, will remain apparent to those skilled in the art, since the generic principles of the present invention is defined to specifically provide a metal detector embedded within a portable medical device and methods using and producing the same as well as new standard of cares making use of the invention.

The present invention provides means for screening subjects for metal containing objects inside them, on their interface or as part of their belongings and their location.

It is within the core concept of the present invention to provide an integrated metal detector-portable medical device adapted to identify metals in a human body, wherein the metal detector is embedded within the portable medical device.

The term "gossypiboma" or "textiloma" refers hereinafter to any surgical complications resulting from foreign materials, such as a surgical sponge, accidentally left inside a patient's body.

The term "metal detector" refers hereinafter to a device which responds to metal that may not be readily apparent. More generally the term refers to any type of metal detector such as Very Low Frequency detectors, Pulse Induction detectors, Beat Frequency Oscillation, etc.

The term "embedded" refers hereinafter to any way the metal detector is connected, interconnected, coupled, joined, implanted, attached, linked or associated to at least one part of the portable medical device.

The term "portable medical device" refers hereinafter to any portable medical device, such as otoscope, stethoscope, CPR Masks, goniometers, thermometer, etc. More generally, the term refers to any medical equipment interfacing the outer (Thermometers, stethoscope, reflex hammer throat illuminator, laryngeal mirror, nasal speculum, tongue depressor, etc.) or inner (endoscopes, laparoscopes, sigmoidoscope, proctoscope, rhinoscope, bronchoscope, otoscope, gynoscope, laparoscope, amnioscope, laryngoscope, esophagoscope, bronchoscope and epiduroscope).

The term "magnetic sensor" refers hereinafter to the metal detector component that first reacts to the presence of metal by emitting a voltage signal (consists of one or more coils).

The term "detectable metals" refers hereinafter to any metal that produces a magnetic field in response to an applied magnetic field such as ferromagnetic (cobalt, iron, nickel, gadolinium, dysprosium, permalloy, awaruite, wairakite, magnetite, etc.) and ferrimagnetic metals.

The term "reporting mechanism" refers hereinafter to at least one way of indication to the user of the metal detector on the presence of detectable metals in or on the subject to be inserted to the MRI machine. Indicators may be audible, visual or sensual.

The term "subject" refers hereinafter to any living substance such as a human or an animal.

The term "distance" refers hereinafter to a description of how far apart the metal detector is from the detectable metal in or on the subject. The term may refer to a physical length or an estimate based on other criteria.

The term "about" refers hereinafter to a range of 25% below or above the referred value.

The term "signal" refers hereinafter to any indicator that serves for means of communication.

The term "audible indicators" refers hereinafter to a representation of sound, typically as an electrical voltage. Audible indicators have frequencies in the audio frequency range of roughly 20 to 20,000 Hz (the limits of human hearing). Audible indicators may be synthesized directly, or may originate at a transducer such as a microphone, musical instrument pickup, phonograph cartridge, or tape head.

The term "visual indicators" refers hereinafter to a representation of light in the visible light range of about 380 nanometers to about 740 nm. More generally the terms refer to any light within the visible range that will be noticeable by the user of the invention (light, flashing light, flickering light, blinking light, change of spectrum of colors of light etc.).

The term "sensible indicators" refers hereinafter to a physical movement of the medical device housing the metal detector which is noticeable to the user (shaking, vibrating, quivering, etc.).

The term "signal intensity" refers hereinafter to the electric-field strength of the electromagnetic wave transmitting the signal.

According to one embodiment of the present invention an integrated metal detector-portable medical device adapted to identify metals in a human body, wherein the metal detector is embedded within the portable medical device is provided.

It is further within the scope of the present invention wherein metal detector provided for identifying metals in a human body, comprising: at least one transmitting means adapted to induce magnetic field generated by the metals to be detected; at least one sensor adapted to detect the magnetic field generated by the metals to be detected; at least one signaling means adapted, upon detection of the magnetic field, to alert the identification of the metals, if the intensity of the magnetic field is above a predetermined value; wherein the metal detector is embedded within a portable medical device.

It is further within the scope of the present invention wherein metal detector as defined in any of the above is provided and wherein the at least one signaling means adapted, upon detection of the magnetic field, to alert the identification of the metals, if the flux of the magnetic field is above a predetermined value.

It is further within the scope of the present invention wherein metal detector as defined in any of the above is provided and wherein the transmitting means are adapted to generate a second magnetic field so as to induce the magnetic field generated by the metal.

It is further within the scope of the present invention wherein metal detector as defined in any of the above is provided and wherein the sensor is at least one radiometer.

It is further within the scope of the present invention wherein metal detector as defined in any of the above is provided and wherein the transmitting means is an antenna or a conductive coil.

It is further within the scope of the present invention wherein metal detector as defined in any of the above is provided and wherein the metal detector comprises at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is further within the scope of the present invention wherein metal detector as defined in any of the above is provided and the same additionally comprises processing means in communication with the first sensor, second sensor and the third sensor, adapted to analyze the first direction, X, second direction, Y, and the third direction, Z so as to determine the 3D position of the metals.

It is further within the scope of the present invention wherein metal detector as defined in any of the above is provided and wherein the 3D position of the metals comprises parameters selected from a group consisting of the 2D location, depth, d, of the metals from the surface of the human body.

It is further within the scope of the present invention wherein metal detector as defined in any of the above is provided and wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is further within the scope of the present invention wherein metal detector as defined in any of the above is provided and wherein the signal is at least one signal selected from a group consisting of (a) audible signal, (b) visual signal, (c) sensual signal, vibration, and any combination thereof.

It is further within the scope of the present invention wherein metal detector as defined in any of the above is provided and wherein the intensity of the signal is in function of at least one parameter selected from a group consisting of depth, d, of the metals from the surface of the human body, the type of the metal, the quantity of the metals and any combination thereof.

It is further within the scope of the present invention wherein metal detector as defined in any of the above is provided and wherein the portable medical device is a stethoscope.

It is further within the scope of the present invention wherein metal detector as defined in any of the above is provided and wherein the stethoscope comprises: (1) at least one chest piece (1), reversibly in contact with the human body; (2) at least one ear tip (2); and (3) a tubing (3) connecting the same.

It is further within the scope of the present invention wherein metal detector as defined in any of the above is provided and wherein the at least one sensor is embedded within at least one selected from a group consisting of the chest piece, the ear tip, the tubing and a combination thereof.

It is further within the scope of the present invention wherein metal detector as defined in any of the above is provided and wherein the at least one signaling means is embedded within at least one selected from a group consisting of the chest piece, the ear tip, the tubing and a combination thereof such that the signal is being activated within the same.

It is further within the scope of the present invention wherein metal detector as defined in any of the above is provided and wherein the signaling means is adapted to alert on detected metals located underneath the surface of a human body.

It is further within the scope of the present invention wherein metal detector as defined in any of the above is provided and wherein the transmitting means comprise means for generating a pulsed magnetic field.

It is further within the scope of the present invention wherein metal detector as defined in any of the above is provided and additionally comprising marking means adapted to mark the surface of the body.

It is further within the scope of the present invention wherein metal detector as defined in any of the above is provided and additionally comprising at least one display for providing a visual indication of the position of the metals in the x-y plane.

It is further within the scope of the present invention wherein metal detector as defined in any of the above is provided and additionally comprising at least one display for providing a visual indication of the position of the metals in the x-y-z planes.

It is further within the scope of the present invention wherein a stethoscope a is provided and comprises at least metal detector, comprising: at least one transmitting means adapted to induce magnetic field generated by the metals to be detected; at least one sensor adapted to detect the magnetic field generated by the metals to be detected; at least one signaling means adapted, upon detection of the magnetic field, to alert the identification of the metals, if the intensity of the magnetic field is above a predetermined value; wherein the metal detector is embedded within the stethoscope.

It is further within the scope of the present invention wherein a stethoscope as defined in any of the above is provided and wherein the stethoscope comprises at least one chest piece (1), reversibly in contact with the human body; at least one ear tip (2); and tubing (3) connecting the same.

It is further within the scope of the present invention wherein a stethoscope as defined in any of the above is provided and wherein the at least one signaling means adapted, upon detection of the magnetic field, to alert the identification of the metals, if the flux of the magnetic field is above a predetermined value.

It is further within the scope of the present invention wherein a stethoscope as defined in any of the above is provided and wherein the transmitting means are adapted to generate a second magnetic field so as to induce the magnetic field generated by the metal.

It is further within the scope of the present invention wherein a stethoscope as defined in any of the above is provided and wherein the sensor is at least one radiometer.

It is further within the scope of the present invention wherein a stethoscope as defined in any of the above is provided and wherein the transmitting means is an antenna or a conductive coil.

It is further within the scope of the present invention wherein a stethoscope as defined in any of the above is provided and wherein the metal detector comprises at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is further within the scope of the present invention wherein a stethoscope as defined in any of the above is provided and wherein the same additionally comprises processing means in communication with the first sensor, second sensor and the third sensor, adapted to analyze the first direction, X, second direction, Y, and the third direction, Z so as to determine the 3D position of the metals.

It is further within the scope of the present invention wherein a stethoscope as defined in any of the above is provided and wherein the 3D position of the metals comprises parameters selected from a group consisting of the 2D location, depth, d, of the metals from the surface of the human body.

It is further within the scope of the present invention wherein a stethoscope as defined in any of the above is provided and wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is further within the scope of the present invention wherein a stethoscope as defined in any of the above is provided and wherein the signal is at least one signal selected from a group consisting of (a) audible signal, (b) visual signal, (c) sensual signal, vibration, and any combination thereof.

It is further within the scope of the present invention wherein a stethoscope as defined in any of the above is provided and wherein the intensity of the signal is in function of at least one parameter selected from a group consisting of depth, d, of the metals from the surface of the human body, the type of the metal, the quantity of the metals and any combination thereof.

It is further within the scope of the present invention wherein a stethoscope as defined in any of the above is provided and wherein the at least one sensor is embedded within at least one selected from a group consisting of the chest piece, the ear tip, the tubing and a combination thereof.

It is further within the scope of the present invention wherein a stethoscope as defined in any of the above is provided and wherein the at least one signaling means is embedded within at least one selected from a group consisting of the chest piece, the ear tip, the tubing and a combination thereof such that the signal is being activated within the same.

It is further within the scope of the present invention wherein a stethoscope as defined in any of the above is provided and wherein the signaling means is adapted to alert on detected metals located underneath the surface of a human body.

It is further within the scope of the present invention wherein a stethoscope as defined in any of the above is provided and wherein the transmitting means comprise means for generating a pulsed magnetic field.

It is further within the scope of the present invention wherein a stethoscope as defined in any of the above is provided and wherein comprising marking means adapted to mark the surface of the body.

It is further within the scope of the present invention wherein a stethoscope as defined in any of the above is provided and wherein the same additionally comprising at least one display for providing a visual indication of the position of the metals in the x-y plane.

It is further within the scope of the present invention wherein a stethoscope as defined in any of the above is provided and wherein the same additionally comprising at least one display for providing a visual indication of the position of the metals in the x-y-z planes.

It is further within the scope of the present invention wherein a portable medical device (100) is provided for the prevention of gossypiboma. This device comprises a distal end and a proximal end interconnect to each other; at least one metal detector for identifying metals underneath a surface of a human body, comprising: at least one transmitting means adapted to induce magnetic field generated by the metals to be detected; at least one sensor adapted to detect the magnetic field generated by the metals to be detected; at least one signaling means; wherein the at least one transmitting means and/or the at least one sensor are embedded either within the distal end or the proximal end; further wherein the signaling means adapted, upon detection of the magnetic field, to alert the identification of the metals, if the intensity of the magnetic field generated is above a predetermined value so as to prevent gossypiboma.

It is further within the scope of the present invention wherein a portable medical device (100) as defined in any of the above is provided and selected from a group consisting of a stethoscope, endoscope and a surgical item, disposable items—sponges, needles, tapes; non-disposable items—graspers, forceps, clamps, occluders, retractors, ribs and other tissue distractors, positioners, stereotactic devices, mechanical cutters scalpels, lancets, drill bits, rasps, trocars, ligasure, harmonic scalpel, dilators and specula, suction tips and tubes, sealing devices, surgical staplers, irrigation and injection needles, tips and tubes, tyndallers, drills, dermatomes; and any combination thereof.

It is further within the scope of the present invention wherein a portable medical device (100) as defined in any of the above is provided wherein the proximal end is located outside the human body and the distal end is reversibly inserted within the body.

It is further within the scope of the present invention wherein a portable medical device (100) as defined in any of the above is provided and is additionally comprising detectable metal indicia embedded within or on the surface of the same; the metal tag is being identified by the metal detector during or after a medical procedure so as to prevent Gossypiboma.

It is further within the scope of the present invention wherein a portable medical device (100) as defined in any of the above is provided and wherein the at least one signaling means adapted, upon detection of the magnetic field, to alert the identification of the metals, if the flux of the magnetic field is above a predetermined value.

It is further within the scope of the present invention wherein a portable medical device (100) as defined in any of the above is provided and wherein the transmitting means are adapted to generate a second magnetic field so as to induce the magnetic field generated by the metal.

It is further within the scope of the present invention wherein a portable medical device (100) as defined in any of the above is provided and wherein the sensor is at least one radiometer.

It is further within the scope of the present invention wherein a portable medical device (100) as defined in any of the above is provided and wherein the transmitting means is an antenna or a conductive coil.

It is further within the scope of the present invention wherein a portable medical device (100) as defined in any of the above is provided and wherein the metal detector comprises at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y.

It is further within the scope of the present invention wherein a portable medical device (100) as defined in any of the above is provided and is additionally comprising processing means in communication with the first sensor, second sensor and the third sensor, adapted to analyze the first direction, X, second direction, Y, and the third direction, Z so as to determine the 3D position of the metals.

It is further within the scope of the present invention wherein a portable medical device (100) as defined in any of the above is provided and wherein the 3D position of the metals comprises parameters selected from a group consisting of the 2D location, depth, d, of the metals from the surface of the human body.

It is further within the scope of the present invention wherein a portable medical device (100) as defined in any of the above is provided and wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is further within the scope of the present invention wherein a portable medical device (100) as defined in any of the above is provided and wherein the signal is at least one signal selected from a group consisting of (a) audible signal, (b) visual signal, (c) sensual signal, vibration, and any combination thereof.

It is further within the scope of the present invention wherein a portable medical device (100) as defined in any of the above is provided and wherein the intensity of the signal is in function of at least one parameter selected from a group consisting of depth, d, of the metals from the surface of the human body, the type of the metal, the quantity of the metals and any combination thereof.

It is further within the scope of the present invention wherein a portable medical device (100) as defined in any of the above is provided and wherein the signaling means is adapted to alert on detected metals located underneath the surface of a human body.

It is further within the scope of the present invention wherein a portable medical device (100) as defined in any of the above is provided and wherein the transmitting means comprise means for generating a pulsed magnetic field.

It is further within the scope of the present invention wherein a portable medical device (100) as defined in any of the above is provided and additionally comprising marking means adapted to mark the surface of the body.

It is further within the scope of the present invention wherein a portable medical device (100) as defined in any of the above is provided and additionally comprising at least one display for providing a visual indication of the position of the metals in the x-y plane.

It is further within the scope of the present invention wherein a portable medical device (100) as defined in any of the above is provided and additionally comprising at least one display for providing a visual indication of the position of the metals in the x-y-z planes.

It is further within the scope of the present invention wherein a method for preventing gossypiboma is provided. This method comprises steps of: providing a metal detector comprising: at least one transmitting means adapted to induce magnetic field generated by the metals to be detected; at least one sensor; at least one signaling means; inducing, during the medical procedure, a magnetic field to be generated by the metals to be detected; sensing the magnetic field; if the intensity of the magnetic field is above a predetermined threshold, identifying the presence of the detectable metals by the magnetic sensor; sending a signal, thereby alerting the detection of the detectable metals; wherein the step of providing the metal detector further comprising step of embedding the metal detector within a portable medical device.

It is further within the scope of the present invention wherein a method for identifying detectable metals in a human body is provided. This method comprises steps of: providing a metal detector comprising: at least one transmitting means adapted to induce magnetic field generated by the metals to be detected; at least one sensor; at least one signaling means; inducing, during the medical procedure, a magnetic field to be generated by the metals to be detected; sensing the magnetic field; if the intensity of the magnetic field is above a predetermined threshold, identifying the presence of the detectable metals by the magnetic sensor; sending a signal, thereby alerting the detection of the detectable metals; wherein the step of providing the metal detector further comprising step of embedding the metal detector within a portable medical device.

It is further within the scope of the present invention wherein the method as defined in any of the above additionally comprises step of generating magnetic field in the vicinity of the metals to be detected thereby inducing the magnetic field generated by the metals to be detected.

It is further within the scope of the present invention wherein the method as defined in any of the above comprises step of generating magnetic field is performed by at least one selected from a group consisting of pulsed magnetic field or an alternating magnetic field, thereby inducing currents within the metals to be detected, thereby generating the magnetic field.

It is further within the scope of the present invention wherein at the method as defined in any of the above at least one signaling means is adapted, upon detection of the magnetic field, to alert the identification of the metals, if the flux of the magnetic field is above a predetermined value.

It is further within the scope of the present invention wherein the method as defined in any of the above additionally comprises step of generating a second magnetic field so as to induce the magnetic field generated by the metal.

It is further within the scope of the present invention wherein the method as defined in any of the above additionally comprises step of selecting the sensor to be at least one radiometer.

It is further within the scope of the present invention wherein the method as defined in any of the above additionally comprises step of selecting the transmitting means from a group consisting of antenna, a conductive coil; and any combination thereof.

It is further within the scope of the present invention wherein the method as defined in any of the above additionally comprises step of providing the metal detector with at least one first sensor, at least one second sensor and at least one third sensor; the at least one first sensor is adapted to detect a first direction, X, of the magnetic field generated by the metals; the at least one second sensor is adapted to detect a second direction, Y, of the magnetic field generated by the metals; the at least one third sensor is adapted to detect a third direction, Z, of the magnetic field generated by the metals; the second direction, Y, is substantially orthogonal to the first direction, X, and the third direction, Z; the first direction, X, is substantially orthogonal to the third direction, Z, and the second direction, Y. According to this embodiment, the metal's 3D position (i.e., the X, Y position and the depth, Z) are calculated and may be provided to the user.

It is further within the scope of the present invention wherein the method as defined in any of the above additionally comprises step of providing processing means in communication with the first sensor, second sensor and the third sensor, adapted to analyze the first direction, X, second direction, Y, and the third direction, Z so as to determine the 3D position of the metals.

It is further within the scope of the present invention wherein the method as defined in any of the above additionally comprises step selecting parameters from a group consisting of the 2D location, depth, d, of the metals from the surface of the human body.

It is further within the scope of the present invention wherein the first sensor is positioned at an angle A relative to the second sensor; the second sensor is positioned at an angle A' relative to the third sensor; the third sensor is positioned at an angle A" relative to the first sensor; where the angles A, A' and A" are in the range of about 0 degrees to about 180 degrees.

It is further within the scope of the present invention wherein the signal is at least one signal selected from a group consisting of (a) audible signal, (b) visual signal, (c) sensual signal, vibration, and any combination thereof.

It is further within the scope of the present invention wherein the intensity of the signal is in function of at least one parameter selected from a group consisting of depth, d, of the metals from the surface of the human body, the type of the metal, the quantity of the metals and any combination thereof.

It is further within the scope of the present invention wherein the portable medical device is a stethoscope.

It is further within the scope of the present invention wherein the stethoscope comprises at least one chest piece (1), reversibly in contact with the human body; at least one ear tip (2); and tubing (3) connecting the same.

It is further within the scope of the present invention wherein the at least one sensor is embedded within at least one selected from a group consisting of the chest piece, the ear tip, the tubing and a combination thereof.

It is further within the scope of the present invention wherein the at least one signaling means is embedded within at least one selected from a group consisting of the chest piece, the ear tip, the tubing and a combination thereof such that the signal is being activated within the same.

It is further within the scope of the present invention wherein the signaling means is adapted to alert on detected metals located underneath the surface of a human body.

It is further within the scope of the present invention wherein the transmitting means comprise means for generating a pulsed magnetic field.

It is further within the scope of the present invention wherein the method additionally comprising step of providing marking means adapted to mark the surface of the body.

It is further within the scope of the present invention wherein the method additionally comprising step of providing at least one display for providing a visual indication of the position of the metals in the x-y plane.

It is further within the scope of the present invention wherein the method additionally comprising step of providing at least one display for providing a visual indication of the position of the metals in the x-y-z planes.

It is further within the scope of the present invention wherein the method additionally comprising step of embedding a metal detector within the portable medical device is adapted to evaluate various parameters of the detectable metals such as their distance from the metal detector, their depth, size and location on a subject.

In order to evaluate these parameters the magnetic sensor of the metal detector has to be composed of 2 oscillators or more. Furthermore, the signaling mechanism of the metal detector is adapted to report on the measurements of the evaluated parameters by producing a signal which its intensity changes as function of at least one of the described parameters or of any combination of them.

The signal can be one or more of audible, visual and sensual parameters that must have the ability to have a range of intensities. For example, a sound that its volume increase in an inverse proportion to the distance of the metal from them metal detector or a vibration that increases in a direct proportion to the size of the metal.

The term "stethoscope" refers hereinafter to an acoustic medical device for auscultation, or listening to the internal sounds of an animal or human body. It operates by the transmission of sound from the chest piece, via air-filled hollow tubes, to the listener's ears. The tubes are also used to carry around the neck when not in use. More generally, the term refers to any kind of stethoscope, e.g., acoustic, electronic, recording, fetoscope and Doppler stethoscope.

It is according to yet another embodiment of the invention, wherein the portable medical device embedding the metal detector to one or more of its parts is a stethoscope. In this embodiment the magnetic sensor is positioned within the chest piece and the user can screen a subject for metals either by directly positioning the chest piece on the body of the subject or by indirectly introducing the stethoscope without directly positioning the chest piece on the user while it is in a resting position, for example, worn on the users neck.

According to the technique chosen for carrying out the detection by the stethoscope an appropriate reporting and/or signaling mechanism is suited: if the user is actively using the stethoscope to check the subject the reporting mechanism is connected to the ear tips of the stethoscope and will be adapted to produce an audible indicator to be heard by the user. If the user is carrying out the detection whilst wearing the stethoscope around the neck the reporting mechanism should be attached to the tubing and be adapted to produce a sensual indicator that can be felt by the user.

It is according to yet another embodiment of the invention, the medical device is provided as defined in any of the above and the reporting and/or signaling mechanism of the metal detector is interconnected to at least one components of the MRI suite consisting of: (1) entrance doors to the restricted zones, (2) control station (3) reception and (4) entrance to the MRI machine and any combination thereof and either: turns on an indicator signal, (2) shuts down and or (3) locks and any combination thereof.

The term "detectable metals in a subject" refers hereinafter to any detectable metal in or on a subject. More generally the term refers to any object that contains detectable metal inside the subject, e.g., pacemaker, implantable cardioverter defibrillator (ICD), neurostimulator, aneurysm clip, metal implant, implanted drug infusion device, foreign metal objects, shrapnel or bullet wounds, permanent cosmetics or tattoos, dentures/teeth with magnetic keepers, other implants that involve magnets, medication patch that contains metal foil, etc. or on its interface: e.g., purse, wallet, money clip, credit cards, cards with magnetic strips, electronic devices such as beepers or cell phones, hearing aids, metal jewelry, watches, pens, paper clips, keys, coins, hair barrettes, hair-pins, any article of clothing that has a metal zipper, buttons, snaps, hooks, underwires, metal threads, shoes, belt buckles, safety pins, etc.

The term "intercommunicate" refers hereinafter to any direct or indirect interaction of the metal detector with the subject by which the first can identify metals in or on the latter.

The term "surgical items" refers hereinafter to instrument and tools used during surgery and placed inside the interior of a subject. More generally the term refers to any disposable item such as sponges, needles, tape etc. and non-disposable item, e.g., graspers, forceps, clamps, occluders, retractors, ribs and other tissue distractors, positioners, stereotactic devices, mechanical cutters scalpels, lancets, drill bits, rasps, trocars, ligasure, harmonic scalpel, dilators and specula, suction tips and tubes, sealing devices, surgical staplers, irrigation and injection needles, tips and tubes, tyndallers, drills, dermatomes etc.

The term "endoscope" refers hereinafter to an instrument used to examine the interior of a hollow organ or cavity of the body, such as esophagogastroduodenoscope, enteroscope, colonoscope, sigmoidoscope, rectoscope, anoscope, proctoscope, rhinoscopy, bronchoscope, otoscope, cystoscopy, gynoscopy, colposcope, hysteroscope, falloposcope, laparoscope, arthroscope, thoracoscope, mediastinoscope, amnioscope, fetoscope, epiduroscope etc. the term also refers a sharp-pointed instrument equipped with a cannula, used to puncture the wall of a body cavity and withdraw fluid, such as trocars, catheters etc.

It is according to yet another embodiment of the invention, wherein the portable medical device embedding the metal detector to one or more of its parts is a laparoscope. In this embodiment the magnetic sensor will be in close proximity to the interior of the subject and therefore positioned at parts of the laparoscope inserted inside the subject such as the end of a channel or the light delivery system. The reporting and/or signaling mechanism is positioned in a place that the signals produced can be easily noticed by the user, therefore, positioned on the eyepiece with a visual indicator or with any external part with an audible indicator.

It is according to yet another object of the invention to disclose a method for screening subjects for detectable metals using a metal detector embedded within a stethoscope wherein the magnetic sensor and the reporting mechanism, adapted to produce an audible indicator, are interconnected to the chest piece and ear tips, respectively. The method inter alia comprises steps of: (a) providing the metal detector, (b) introducing at least one of the ear tips to at least one ear of the user, (c) contacting the chest piece to the subject to be screened, (d) moving the chest piece along the surface of the subject and (e) listening to the audible indicators and their intensities to identify and locate the detectable metals.

It is according to yet another object of the invention to disclose a method for screening subjects for detectable metals using a metal detector embedded within a stethoscope wherein the magnetic sensor and the reporting mechanism, adapted to produce a sensual indicator, are interconnected to the chest piece and tubing, respectively. The method inter alia comprises steps of: (a) providing the metal detector, (b) wearing the stethoscope around the neck of the user, (c) approaching the subject to be screened, (d) moving around the subject and (e) focusing on the sensual indicators and their intensities to identify and locate the detectable metals.

It is according to yet another object of the invention to disclose a method for using the metal detector embedded within a laparoscope wherein the magnetic sensor and the reporting mechanism are located in the parts residing in the interior of the subject and the parts residing in the exterior of the subject, respectively. The method inter alia comprises steps of: (a) providing the metal detector, (b) introducing the metal detector to the interior of the subject and (c) keeping track of the indicators signaling for metals especially before finishing the procedure.

Figure 1:
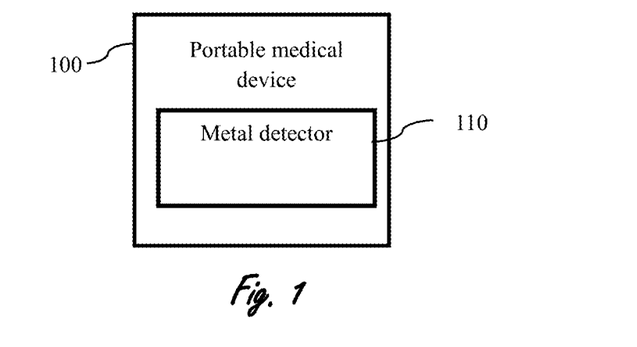

Reference is now made to FIG. 1, shown is a schematic view of the present invention. The portable medical device (100) includes within it a metal detector (110) for identifying detectable metals.

Figure 2:
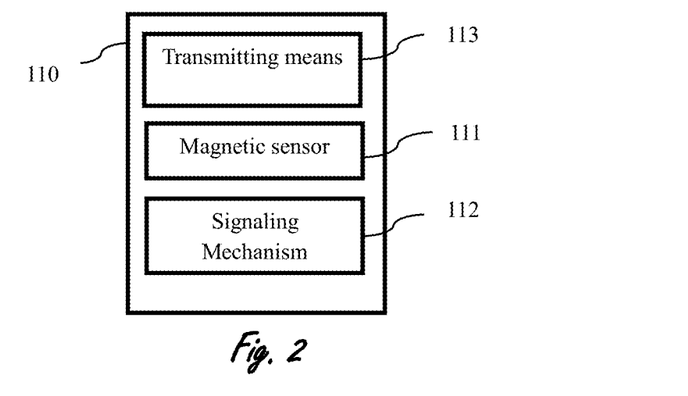
FIG. 2 schematically illustrates the metal detector of the present invention.
Figure 2A:
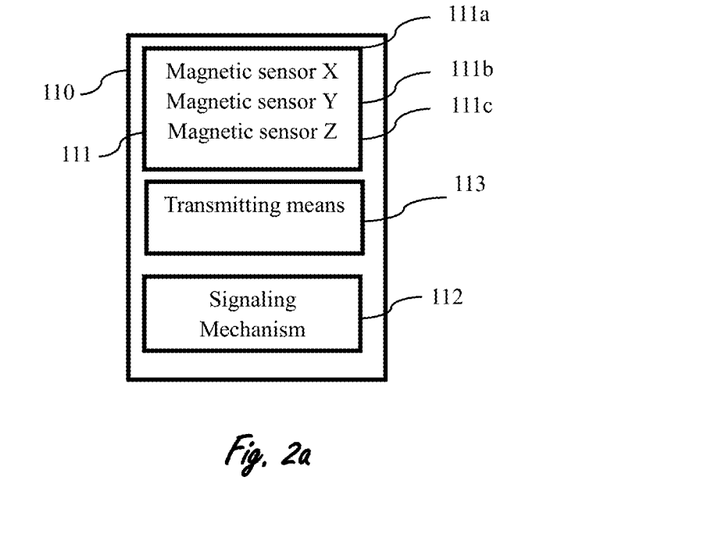
FIG. 2a schematically illustrates a three-sensors embodiment of the metal detector of the present invention.

Reference is now made to FIG. 2, shown is a schematic view of the metal detector (110) which is comprised of three parts: a magnetic sensor (111) that identifies detectable metals, a transmitting means 113 adapted to induce magnetic field generated by the metals to be detected and a signaling mechanism (112). The signaling mechanism (112) is activated in response to the presence of the detectable metals. FIG. 2*a* illustrates a three-sensor embodiment of the metal detector of the present invention according to which, sensors 111*a*, 111*b* and 111*c* are adapted to detect magnetic fields in three directions orthogonal to each other.

Figure 3:
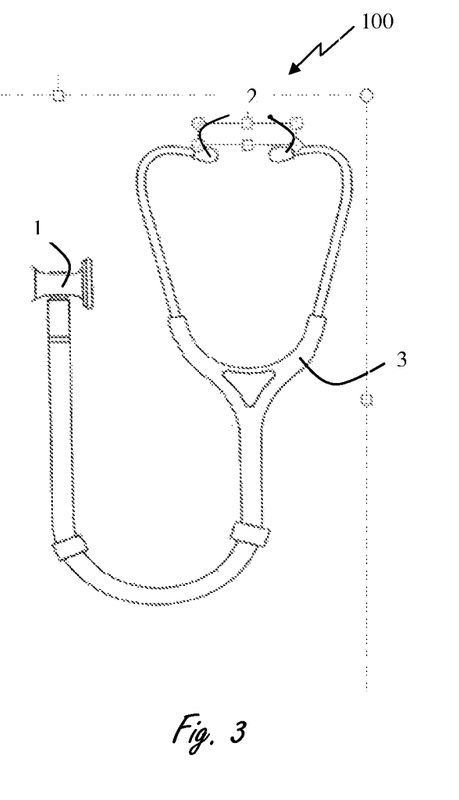
FIGS. 3-5 schematically illustrate a stethoscope according to the present invention.

Reference is now made to FIG. 3, shown an illustrative view of a stethoscope which is a possible portable medical device which may be adapted to house a metal detector. The stethoscope (100) is comprised of a chest piece (1), ear tips (2) and tubing (3) connecting them. All those three modules of the stethoscope are possible candidates for housing one or more of the metal detectors components.

Figure 4:
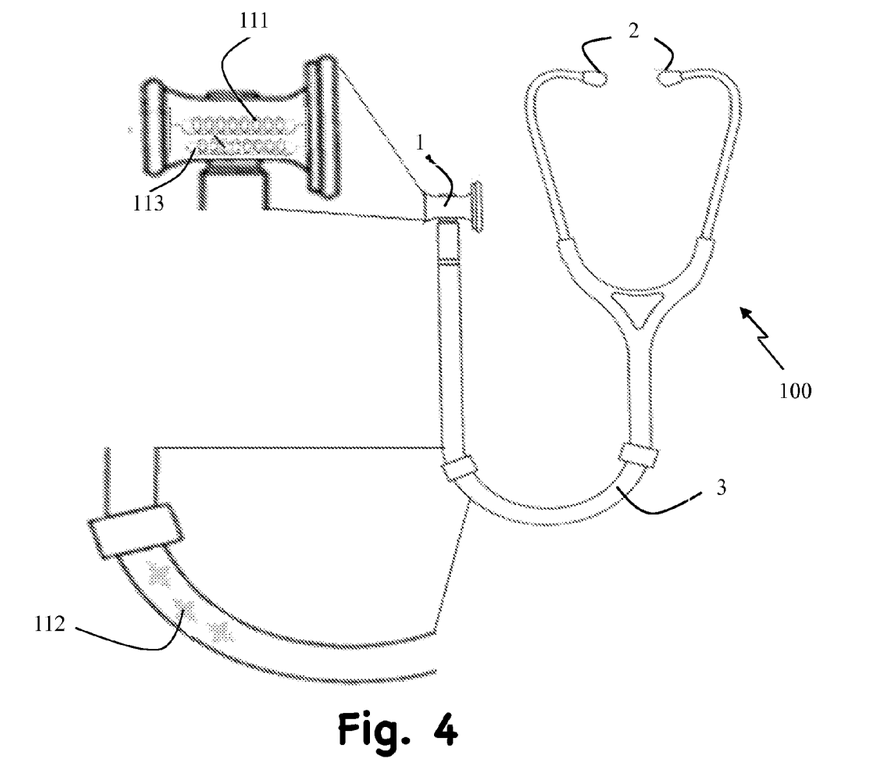

Reference is now made to FIG. 4, shown an illustrate of one embodiment of the invention in which the medical device is a stethoscope (100) housing a metal detector, which is interconnected to 2 modules of the stethoscope: the transmitter (113), embodied as a conductive coil, and the magnetic sensor (111) are embedded within the chest piece (1) and the detectable metal reporting (signaling) mechanism (112) resides within the tubing (3). In this embodiment the signal produced by the detectable metal reporting mechanism is sensible and can be felt by the user as vibrations when wore around the neck.

Figure 5:
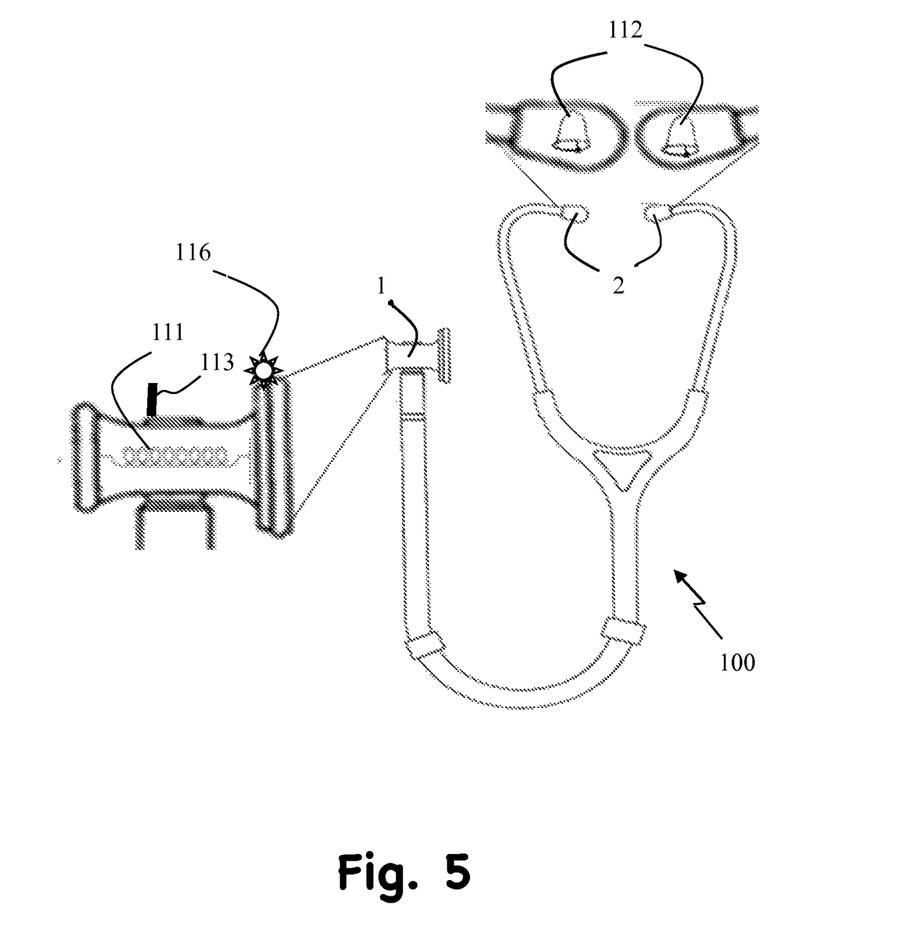

Reference is now made to FIG. 5, shown an illustrate of yet another embodiment of the invention in which the medical device is a stethoscope (100) housing a metal detector, which is interconnected to 2 modules of the stethoscope: the magnetic sensor (111) is embedded within the chest piece (1), the transmitting means (113), embodied as an antenna, is connected to the chest piece, and the detectable metal reporting (signaling) mechanism (112) resides within the ear tips (2). In this embodiment the signal produced by the detectable metal reporting mechanism is audible and can be heard by the user as beeping sounds when ear tips are inserted inside the ears. Alternatively, or additionally, stethoscope (100) may comprise a visual signaling means (116) which produces a visual signal upon detection of a metallic object.

According to one embodiment of the present invention the metal detector is operated according to at least one of the following protocols: Very low frequency (VLF); Pulse induction (PI); Beat-frequency oscillation (BFO) or any combination thereof. Each of which will be briefly discussed herein below:

In a VLF metal detector, also known as induction balance, there are two distinct coils:

Transmitter coil—This is the outer coil loop. Within it is a coil of wire. Electricity is sent along this wire, first in one direction and then in the other, thousands of times each second. The number of times that the current's direction switches each second establishes the frequency of the unit.

Receiver coil—This inner coil loop contains another coil of wire. This wire acts as an antenna to pick up and amplify frequencies coming from target objects in the ground.

The current moving through the transmitter coil creates an electromagnetic field. Each time the current changes direction, the polarity of the magnetic field changes.

As the magnetic field pulses back and forth into the ground, it interacts with any conductive objects it encounters, causing them to generate weak magnetic fields of their own. The object's magnetic field is directly opposite the transmitter coil's magnetic field. If the transmitter coil's field is pulsing downward, the object's field is pulsing upward.

The receiver coil is completely shielded from the magnetic field generated by the transmitter coil. However, it is not shielded from magnetic fields coming from objects in the ground. Therefore, when the receiver coil passes over an object giving off a magnetic field, a small electric current travels through the coil. This current oscillates at the same frequency as the object's magnetic field. The coil amplifies the frequency and sends it to the control box of the metal detector, where sensors analyze the signal.

According to the strength of the magnetic field, the metal detector can estimate at what depth the metals detected are located.

The VLF metal detector is based on phase shifting. I.e., the difference in timing between the transmitter coil's frequency and the frequency of the target object.

The pulse induction (PI) based metal detector, uses a single coil as both transmitter and receiver, or they may have two or even three coils working together. According to this embodiment, powerful, short bursts (pulses) of current are sent through a coil of wire.

Each pulse generates a brief magnetic field. When the pulse ends, the magnetic field reverses polarity and collapses suddenly, resulting in a sharp electrical spike. This spike causes another current to run through the coil. This current is called the reflected pulse and is extremely short. Another pulse is then sent and the process repeats.

According to this embodiment, if the metal detector detects a metal, the pulse creates an opposite magnetic field in the object. When the pulse's magnetic field collapses, causing the reflected pulse, the magnetic field of the metal object makes it take longer for the reflected pulse to completely disappear.

In the beat-frequency oscillator (BFO) based metal detectors, there are two coils of wire. One large coil, and a smaller coil. Each coil is connected to an oscillator that generates thousands of pulses of current per second. The frequency of these pulses is slightly offset between the two coils.

As the pulses travel through each coil, the coil generates radio waves. A tiny receiver within the control box picks up the radio waves and creates an audible series of tones (beats) based on the difference between the frequencies.

If the large coil passes over a metal object, the magnetic field caused by the current flowing through the coil creates a magnetic field around the object. The object's magnetic field interferes with the frequency of the radio waves generated by the large coil. As the frequency deviates from the frequency of the smaller coil, the audible beats change in duration and tone.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

It is according to one embodiment of the invention, wherein a metal detector for identifying metals in a human body and/or underneath the surface of the human body, is embedded to a portable medical device. The metal detector comprises: at least one transmitting means adapted to generate a second magnetic field so as to induce the magnetic field generated by the metal, selected from a group consisting of: (1) antenna; (2) conductive coil; and any combination thereof; at least one sensor adapted to detect the magnetic field generated by metals to be detected; and at least one signaling means adapted, upon detection of the magnetic field, to alert the identification of metals, if the intensity of the magnetic field is above a predetermined value.

It is according to another embodiment of the invention, wherein a metal detector for identifying metals in a human body and/or underneath the surface of the human body is used for the prevention of gossypiboma. The metal detector comprises: at least one transmitting means adapted to induce magnetic field generated by metals to be detected, selected from a group consisting of: (1) antenna; (2) conductive coil; and any combination thereof; at least one sensor adapted to detect the magnetic field generated by metals to be detected; at least one signaling means; wherein at least one transmitting means and/or at least one sensor are embedded within either the distal end or the proximal end of a portable medical device. The signaling means are adapted, upon detection of the magnetic field, to alert on the identification of the metals, if the intensity of the magnetic field generated is above a predetermined value so as to prevent gossypiboma.

In yet another embodiment of the invention the sensor is at least one radiometer.

In yet another embodiment of the invention the signal is at least one signal selected from a group consisting of (a) audible signal, (b) visual signal, (c) sensible signal, and any combination thereof.

In yet another embodiment of the invention the intensity of the signal is in function of at least one parameter selected from a group consisting of: depth of the metals from the surface of the human body, the type of the metal, the quantity of the metals, and any combination thereof.

In yet another embodiment of the invention the transmitting means are adapted to generate a second magnetic field so as to induce the magnetic field generated by the metal.

In yet another embodiment of the invention at least one signaling means adapted, upon detection of the magnetic field, to alert the identification of metals, if the flux of the magnetic field is above a predetermined value.

In yet another embodiment of the invention the transmitting means comprise means for generating a pulsed magnetic field.

In yet another embodiment of the invention the portable medical device is a stethoscope, comprising: at least one chest piece (1), reversibly in contact with a human body; at least one ear tip (2); and tubing (3) connecting the same.

In yet another embodiment of the invention at least one sensor and at least one signaling means are embedded within at least one selected from a group consisting of: chest piece, ear tip, tubing and a combination thereof.

In yet another embodiment of the invention the portable medical device is selected from a group consisting of: (1) stethoscope, (2) endoscope; (3) surgical item (graspers, forceps, clamps, occluders, retractors, ribs and other tissue distractors, positioners, stereotactic devices, mechanical cutters scalpels, lancets, drill bits, rasps, trocars, ligasure, harmonic scalpel, dilators and specula, suction tips and tubes, sealing devices, surgical staplers, irrigation and injection needles, tips and tubes, tyndallers, drills, dermatomes); and any combination thereof.

In yet another embodiment of the invention the portable medical device wherein the proximal end is located outside the human body and the distal end is reversibly inserted within the body.

In yet another embodiment of the invention a method for preventing gossypiboma during a medical procedure, comprises steps of: providing a metal detector comprising: at least one transmitting means adapted to induce magnetic field generated by metals to be detected; at least one sensor; at least one signaling means; inducing, during a medical procedure, a magnetic field to be generated by metals to be detected; sensing the magnetic field; if the intensity of the magnetic field is above a predetermined threshold, identifying the presence of the detectable metals by the magnetic sensor; and sending a signal, thereby alerting the detection of detectable metals; wherein the step of providing the metal detector further comprising step of embedding the metal detector within a portable medical device.

In yet another embodiment of the invention a method for identifying detectable metals in a human body and underneath the surface of the human, comprises steps of providing a metal detector comprising: at least one transmitting means adapted to induce magnetic field generated by metals to be detected selected from a group consisting of: (1) antenna; (2) conductive coil; and any combination thereof; at least one sensor; at least one signaling means; inducing a magnetic field to be generated by the metals to be detected; sensing the magnetic field; if the intensity of the magnetic field is above a predetermined threshold, identifying the presence of the detectable metals by the magnetic sensor; sending a signal, thereby alerting the detection of the detectable metals; wherein the step of providing the metal detector further comprising step of embedding the metal detector within a portable medical device.

The methods according to the previous embodiments additionally comprising step of generating magnetic field in the vicinity of the metals to be detected thereby inducing the magnetic field generated by the metals to be detected.

The methods according to the previous embodiments wherein the step of generating magnetic field is performed by at least one selected from a group consisting of pulsed magnetic field or an alternating magnetic field, thereby inducing currents within the metals to be detected, thereby generating the magnetic field.

The methods according to the previous embodiments wherein at least one signaling means adapted, upon detection of the magnetic field, to alert the identification of metals, if the flux of the magnetic field is above a predetermined value.

The methods according to the previous embodiments additionally comprising step of selecting a sensor to be at least one radiometer.

The methods according to the previous embodiments wherein the signal is at least one signal selected from a group consisting of (a) audible signal, (b) visual signal, (c) sensible signal, and any combination thereof.

The methods according to the previous embodiments wherein the intensity of the signal is in function of at least one parameter selected from a group consisting of depth of the metals from the surface of the human body, the type of the metal, the quantity of the metals and any combination thereof.

The methods according to the previous embodiments wherein the portable medical device is a stethoscope, comprises: at least one chest piece (1), reversibly in contact with the human body; at least one ear tip (2); and tubing (3) connecting the same.

The methods according to the previous embodiments wherein at least one sensor and at least one signaling means are embedded within at least one selected from a group consisting of the chest piece, the ear tip, the tubing and a combination thereof.

The methods according to the previous embodiments wherein the transmitting means comprise means for generating a pulsed magnetic field.

The invention claimed is:

1. An integrated stethoscope-metal detector device for screening a human body for metals, comprising:
    a stethoscope comprising a chest piece, at least one ear tip and a tubing connecting between said chest piece and said at least one ear tip; and
    a metal detector embedded within said stethoscope, said metal detector comprising a transmitting means adapted to induce a magnetic field in metals, a sensor for detecting said magnetic field and a signaling means, in communication with said sensor, said signaling means is configured to send an alert signal when a magnetic field of an intensity above a predetermined threshold is detected by said sensor.

2. The integrated stethoscope-metal detector device according to claim 1 wherein said transmitting device is selected from a group consisting of: (i) an antenna; (ii) a conductive coil; and any combination thereof.

3. The integrated stethoscope-metal detector device according to claim 1 wherein said transmitting means and said sensor are embedded in said chest piece and wherein said signaling means are embedded within said at least one ear tip or said tubing.

4. The integrated stethoscope-metal detector device according claim 1, wherein said signaling means is configured to send said alert signal as a signal selected from the group consisting of an audible signal, a visual signal, a sensual signal, and any combination thereof.

5. The integrated stethoscope-metal detector device according to claim 1, wherein said signaling means is embedded within said at least one ear tip and wherein said alert signal is an audible signal.

6. The integrated stethoscope-metal detector device according to claim 1 wherein said signaling means is embedded within the tubing and wherein said alert signal is a vibration sensible by a user when said stethoscope is worn around the user's neck.

7. The integrated stethoscope-metal detector device according to claim 1 wherein the metal detector is configured to operate according to one of the following protocols: a Very low frequency (VLF) protocol, a Pulse induction (PI) protocol and a Beat-frequency oscillation (BFO) protocol.

8. The integrated stethoscope-metal detector device according to claim 1, wherein said transmitting means comprises means for generating a pulsed magnetic field, an alternating magnetic field or a combination thereof.

9. The integrated stethoscope-metal detector device according to claim 1 wherein said metal detector comprises a first sensor adapted to detect a first direction of said magnetic field, a second sensor adapted to detect a second direction of said magnetic field and a third sensor adapted to detect a third direction of said magnetic field, wherein said second direction is orthogonal to said first direction and said third direction is orthogonal to said first and second directions.

10. The integrated stethoscope-metal detector device according claim 1, wherein said signaling means is configured to send said alert signal with an intensity which is a function of at least one parameter selected from a group consisting of a depth of said metal from a surface of said human body, a type of said metal, a quantity of said metal, and any combination thereof.

\* \* \* \* \*